United States Patent
Smith et al.

(10) Patent No.: US 8,696,635 B2
(45) Date of Patent: Apr. 15, 2014

(54) INTRODUCER SEAL ASSEMBLY WITH LOW PROFILE GIMBAL SEAL

(75) Inventors: Robert C. Smith, Cheshire, CT (US); Thomas Wenchell, Durham, CT (US)

(73) Assignee: Covidien LP, Mansfield, MA (US)

( * ) Notice: Subject to any disclaimer, the term of this patent is extended or adjusted under 35 U.S.C. 154(b) by 339 days.

(21) Appl. No.: 13/050,987

(22) Filed: Mar. 18, 2011

(65) Prior Publication Data

US 2011/0201891 A1    Aug. 18, 2011

Related U.S. Application Data

(63) Continuation of application No. 11/098,966, filed on Apr. 5, 2005, now Pat. No. 7,931,624.

(51) Int. Cl.
*A61M 5/178* (2006.01)

(52) U.S. Cl.
USPC .................................................. 604/167.03

(58) Field of Classification Search
USPC ........................................ 604/167.01–167.06
See application file for complete search history.

(56) References Cited

U.S. PATENT DOCUMENTS

| | | | |
|---|---|---|---|
| 3,421,509 A | 1/1969 | Fiore | |
| 3,565,078 A | 2/1971 | Vailliancourt et al. | |
| 3,853,127 A | 12/1974 | Spademan | |
| 3,907,310 A | 9/1975 | Dufour | |
| 3,994,287 A | 11/1976 | Turp et al. | |
| 4,000,739 A | 1/1977 | Stevens | |
| 4,112,932 A | 9/1978 | Chiulli | |
| 4,173,350 A | 11/1979 | Sieghartner | |
| 4,177,814 A | 12/1979 | Knepshield et al. | |
| 4,177,997 A | 12/1979 | Cartwright | |
| 4,240,335 A | 12/1980 | Stucka et al. | |
| 4,240,411 A | 12/1980 | Hosono | |
| 4,311,315 A | 1/1982 | Kronenberg | |
| 4,334,688 A | 6/1982 | Spargo et al. | |

(Continued)

FOREIGN PATENT DOCUMENTS

| | | |
|---|---|---|
| DE | 1893771 | 5/1964 |
| DE | 3217118 | 8/1983 |

(Continued)

OTHER PUBLICATIONS

European Search Report for corresponding EP09250324 dated Jul. 25, 2011.

(Continued)

*Primary Examiner* — Nicholas Lucchesi
*Assistant Examiner* — Pritesh Patel

(57) ABSTRACT

A surgical seal assembly for use with a surgical access device includes a seal housing defining a central longitudinal axis and having a longitudinal passage dimensioned to permit passage of a surgical instrument through the seal housing, a gimbal mount disposed within the seal housing and having a gimbal seal member defining an aperture for substantial sealed reception of the surgical instrument, and an interface seal disposed within the seal housing. The gimbal mount is adapted for angular movement relative to the central longitudinal axis upon angulation of the surgical instrument whereby the gimbal seal member substantially maintains the sealed reception of the surgical instrument. The interface seal includes an interface seal member extending at least along the longitudinal axis and being in substantial contacting sealing relation with the gimbal mount. The interface seal member is adapted to maintain the sealing relation with the gimbal mount upon angular movement thereof.

11 Claims, 9 Drawing Sheets

(56) References Cited

U.S. PATENT DOCUMENTS

| | | | |
|---|---|---|---|
| 4,338,689 A | 7/1982 | Zieg | |
| 4,383,692 A | 5/1983 | Proctor | |
| 4,386,756 A | 6/1983 | Muchow | |
| 4,387,879 A | 6/1983 | Tauschinski | |
| 4,430,081 A | 2/1984 | Timmermans | |
| 4,447,237 A | 5/1984 | Frisch et al. | |
| 4,448,449 A | 5/1984 | Halling et al. | |
| 4,464,178 A | 8/1984 | Dalton | |
| 4,553,760 A | 11/1985 | Reed et al. | |
| 4,588,195 A | 5/1986 | Antonini et al. | |
| 4,601,710 A | 7/1986 | Moll | |
| 4,626,245 A | 12/1986 | Weinstein | |
| 4,641,842 A | 2/1987 | Kataoka | |
| 4,654,030 A | 3/1987 | Moll et al. | |
| 4,655,752 A | 4/1987 | Honkanen et al. | |
| 4,673,393 A | 6/1987 | Suzuki et al. | |
| 4,705,511 A | 11/1987 | Kocak | |
| 4,715,360 A | 12/1987 | Akui et al. | |
| 4,723,550 A | 2/1988 | Bales et al. | |
| 4,758,225 A | 7/1988 | Cox et al. | |
| 4,795,439 A | 1/1989 | Guest | |
| 4,842,591 A | 6/1989 | Luther | |
| 4,844,483 A | 7/1989 | Iijima et al. | |
| 4,844,484 A | 7/1989 | Antonini et al. | |
| 4,857,062 A | 8/1989 | Russell | |
| 4,869,717 A | 9/1989 | Adair | |
| 4,889,349 A | 12/1989 | Muller | |
| 4,909,798 A | 3/1990 | Fleischhacker et al. | |
| 4,912,287 A | 3/1990 | Ono et al. | |
| 4,932,633 A | 6/1990 | Johnson et al. | |
| 4,943,280 A | 7/1990 | Lander | |
| 4,966,588 A | 10/1990 | Rayman et al. | |
| 4,998,740 A | 3/1991 | Tellier | |
| 5,000,745 A | 3/1991 | Guest et al. | |
| 5,002,557 A | 3/1991 | Hasson | |
| 5,015,000 A | 5/1991 | Perini | |
| 5,038,756 A | 8/1991 | Kepley | |
| 5,041,095 A | 8/1991 | Littrell | |
| 5,053,014 A | 10/1991 | Van Heugten | |
| 5,053,016 A | 10/1991 | Lander | |
| 5,073,169 A | 12/1991 | Raiken | |
| 5,104,383 A | 4/1992 | Shichman | |
| 5,123,634 A | 6/1992 | Schwerdt | |
| 5,137,520 A | 8/1992 | Maxson et al. | |
| 5,167,636 A | 12/1992 | Clement | |
| 5,180,373 A | 1/1993 | Green et al. | |
| 5,211,370 A | 5/1993 | Powers | |
| 5,226,891 A | 7/1993 | Bushatz et al. | |
| 5,273,545 A | 12/1993 | Hunt et al. | |
| 5,290,304 A | 3/1994 | Storace | |
| 5,299,813 A | 4/1994 | McKenna | |
| 5,300,036 A | 4/1994 | Mueller et al. | |
| 5,342,315 A | 8/1994 | Rowe et al. | |
| 5,385,553 A | 1/1995 | Hart | |
| 5,499,823 A | 3/1996 | Fukui | |
| 5,603,702 A | 2/1997 | Smith et al. | |
| 5,614,136 A | 3/1997 | Pepin | |
| 5,685,854 A | 11/1997 | Green et al. | |
| 5,720,759 A * | 2/1998 | Green et al. | 606/167 |
| 5,779,697 A | 7/1998 | Glowa | |
| 5,792,113 A | 8/1998 | Kramer et al. | |
| 5,820,600 A * | 10/1998 | Carlson et al. | 604/167.03 |
| 5,839,639 A | 11/1998 | Sauer et al. | |
| 6,039,725 A | 3/2000 | Moenning et al. | |
| 6,113,106 A | 9/2000 | Dahlheimer | |
| 6,231,565 B1 | 5/2001 | Tovey et al. | |
| 6,440,063 B1 | 8/2002 | Beane et al. | |
| 6,663,614 B1 | 12/2003 | Carter | |
| 2004/0066008 A1 | 4/2004 | Smith | |
| 2004/0204682 A1 | 10/2004 | Smith | |

FOREIGN PATENT DOCUMENTS

| | | |
|---|---|---|
| EP | 0029864 | 6/1981 |
| EP | 0051718 | 5/1982 |
| EP | 0113520 | 7/1984 |
| EP | 0312219 | 4/1989 |
| EP | 0550069 A1 | 7/1993 |
| EP | 1707133 A1 | 10/2006 |
| GB | 1482857 | 8/1977 |
| GB | 2298905 | 9/1996 |
| WO | WO 93 04717 | 3/1993 |
| WO | WO94/04067 A1 | 3/1994 |
| WO | WO 97 42991 | 11/1997 |
| WO | WO 98 53865 | 12/1998 |
| WO | WO 98/53865 | 12/1998 |
| WO | WO02/17800 A2 | 3/2002 |
| WO | WO 02/41795 | 5/2002 |
| WO | WO 03/094760 | 11/2003 |
| WO | WO 03094760 | 11/2003 |
| WO | WO2006/110733 A2 | 10/2006 |
| WO | WO2008/121294 A1 | 10/2008 |
| WO | WO2008/149332 A1 | 12/2008 |

OTHER PUBLICATIONS

European Search Report for EP 06006537, date of completion Jun. 16, 2006 (8 pgs).

European Search Report—Application No. EP 06 00 4113, dated Jun. 13, 2006.

International Search Report—Application No. PCT/US03/12894, dated Nov. 17, 2003.

\* cited by examiner

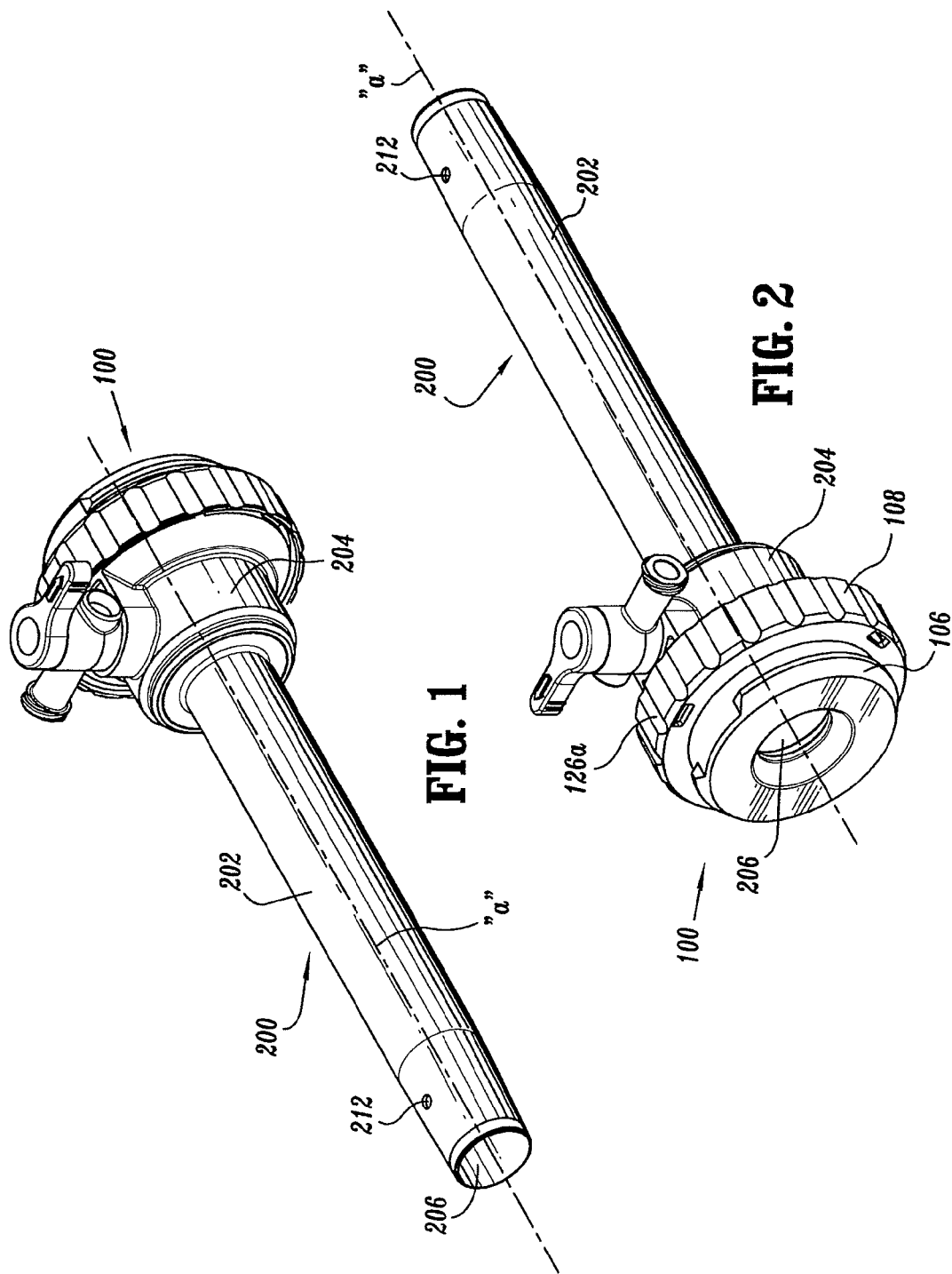

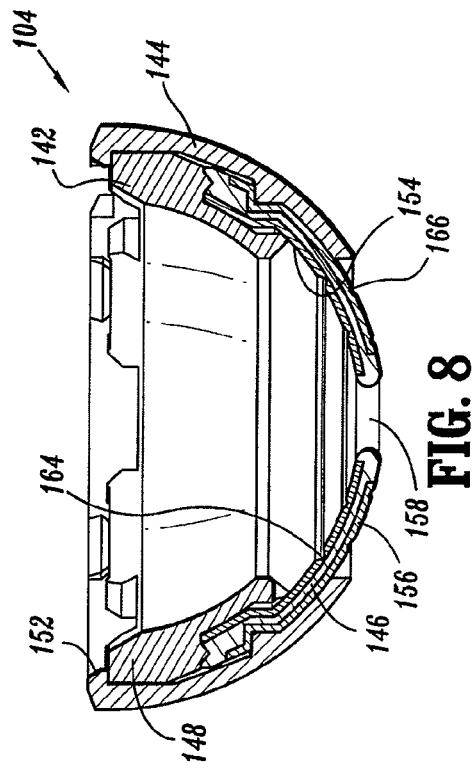
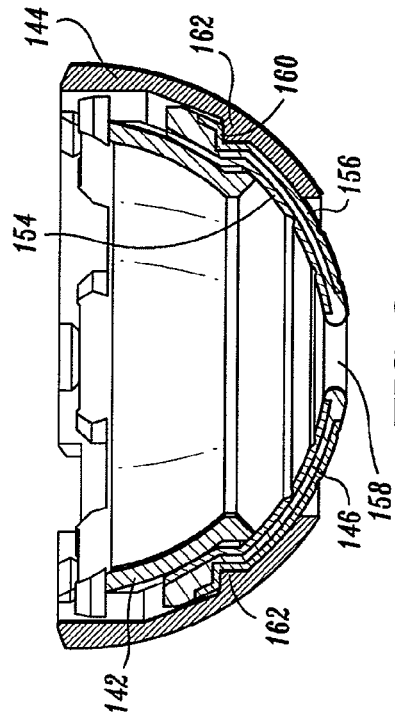
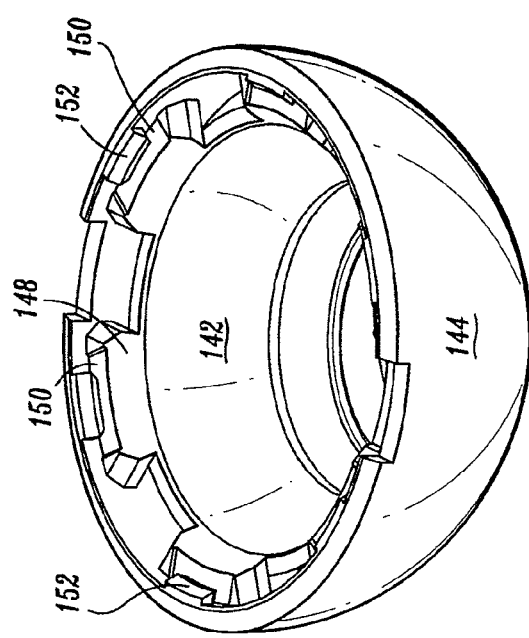
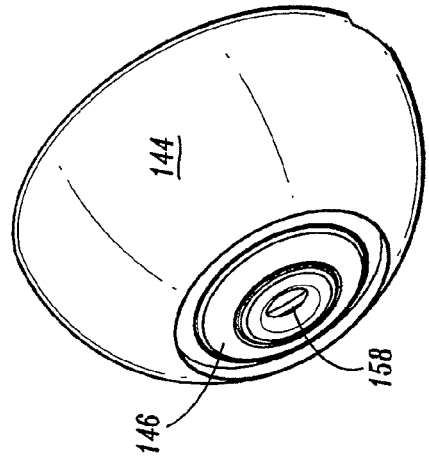
FIG. 6
FIG. 7
FIG. 8
FIG. 9

INTRODUCER SEAL ASSEMBLY WITH LOW PROFILE GIMBAL SEAL

CROSS-REFERENCE TO RELATED APPLICATIONS

The present application is a continuation of U.S. patent application Ser. No. 11/098,966, filed Apr. 5, 2005, now U.S. Pat. No. 7,931,624, the entire contents of which are hereby incorporated by reference.

BACKGROUND

1. Technical Field

The present disclosure relates to a seal system adapted to permit the introduction of surgical instrumentation into a patient's body. In particular, the present disclosure relates to a seal system for use with an introducer or access device which is intended for insertion into a patient's body, and to receive an instrument in sealing engagement therewith.

2. Description of the Related Art

Minimally invasive and laparoscopic procedures generally require that any instrumentation inserted into the body is sealed, i.e., provisions must be made to ensure that gases and/or fluids do not enter or exit the body through an endoscopic incision, such as, for example in surgical procedures where the surgical region is insufflated. For such procedures, the introduction of a tube into anatomical cavities, such as the peritoneal cavity, is usually accomplished by use of a system incorporating a trocar and cannula assembly. Since the cannula is in direct communication with the interior of the peritoneal cavity, insertion of the cannula into an opening in the patient's body to reach the inner abdominal cavity should be adapted to maintain a fluid tight interface between the abdominal cavity and the outside atmosphere. In view of the need to maintain the atmospheric integrity of the inner area of the cavity, a seal assembly for a cannula, which permits introduction of a wide range of surgical instrumentation and maintains the atmospheric integrity of the inner area of the cavity, is desirable. In this regard, there have been a number of attempts in the prior art to achieve such sealing requirements. A difficulty encountered with conventional seal assemblies, however, is the inability of accommodating the wide range of sizes of instrumentation. In addition, angulation and/or manipulation of instrumentation within the cannula often present difficulties with respect to maintaining seal integrity.

SUMMARY

Accordingly, the present disclosure provides a seal assembly which will allow a surgeon to efficaciously utilize instruments of varying diameter in a surgical procedure. This seal assembly obviates the need for multiple adapters to accommodate instruments of varying diameter by providing an apertured resilient seal member which is mounted in a gimbal-like assembly. In one preferred embodiment, a surgical seal assembly for use with a surgical access device, includes a seal housing defining a central longitudinal axis and having a longitudinal passage dimensioned to permit passage of a surgical instrument through the seal housing, a gimbal mount disposed within the seal housing and having a gimbal seal member defining an aperture for substantial sealed reception of the surgical instrument, and an interface seal disposed within the seal housing. The gimbal mount is adapted for angular movement relative to the central longitudinal axis upon angulation of the surgical instrument whereby the gimbal seal member substantially maintains the sealed reception of the surgical instrument. The interface seal includes a resilient interface seal member extending at least along the longitudinal axis and being in substantial contacting sealing relation with the gimbal mount. The interface seal member is adapted to maintain the sealing relation with the gimbal mount upon angular movement thereof.

One preferred interface seal includes a relatively rigid interface mount whereby the interface seal member is mounted to the interface mount. The interface seal may include an annular gasket seal member mounted to the interface mount and positioned to contact an internal surface of the seal housing in substantial sealing relation therewith to form a substantial seal within the seal housing. The interface seal member and the gasket seal member may be monolithically formed. The gasket seal member is mounted adjacent a proximal side of the interface mount and the interface seal member is mounted adjacent a distal side of the interface mount.

The seal housing includes an interior wall portion at least partially defining the longitudinal passage. The interior wall portion is disposed in oblique relation relative to the longitudinal axis to taper radially inwardly along the longitudinal axis to facilitate reception of the surgical instrument. The interior wall portion is adjacent a proximal end of the seal housing. The interior wall portion permits the surgeon to introduce an instrument without concern that the instrument be in substantial alignment with the longitudinal axis of the seal housing.

The preferred seal housing defines a reduced profile having a height ranging from about 0.25 inches to about 1.0 inches, preferably, 0.65 inches.

The gimbal seal member may include a resilient member and a protective layer juxtaposed relative to the resilient member. The protective layer of the gimbal seal member extends at least partially within the aperture to protect portions of the seal member defining the aperture during passage of the surgical instrument. The protective layer may include a fabric material.

In another preferred embodiment, the surgical seal assembly for use with a surgical access device includes a low profile seal housing defining a central longitudinal axis and having an internal wall defining a longitudinal passage dimensioned to permit passage of a surgical instrument through the seal housing, a gimbal mount disposed within the seal housing and having a gimbal seal member defining an aperture for substantial sealed reception of the surgical instrument, and an interface seal disposed within the seal housing. The internal wall of the seal housing defines a tapered internal wall portion dimensioned to receive the surgical instrument when inserted within the longitudinal passage in angulated relation thereto. The interface seal includes an annular interface seal mount and an interface seal member mounted to the interface seal mount. The interface seal member extends at least radially inwardly relative to the longitudinal axis to contact the gimbal mount and form a substantial seal therewith. The interface seal member is adapted to maintain the sealing relation with the gimbal mount upon angular movement thereof. The gimbal mount is adapted for angular movement relative to the central longitudinal axis upon angulation of the surgical instrument whereby the gimbal seal member substantially maintains the sealed reception of the surgical instrument. The preferred seal housing defines a height ranging from about 0.25 inches to about 1.0 inches.

The preferred seal housing defines an arcuate channel portion for at least partially accommodating the gimbal mount. The gimbal mount is adapted to traverse the arcuate channel portion. The interface seal member may be dimensioned to extend along the central longitudinal axis of the seal housing.

The interface seal may include an annular gasket seal member mounted to the interface mount and positioned to contact an internal surface of the seal housing in substantial sealing relation therewith to form a substantial seal within the seal housing. The seal housing is adapted to be detachably mounted to a cannula assembly.

The movement of the gimbal mount relative to the housing which is accommodated by the gimbal-like structure also facilitates seal maintenance once an instrument is being used within the body cavity. In particular, as an instrument is manipulated, the gimbal seal member repositions itself through movement of the gimbal mount relative to the seal housing, thereby ensuring that the gimbal seal member maintains a fluid-tight seal around the instrument shaft.

Other features and advantages of the present disclosure will become apparent from the following detailed description, taken in conjunction with the accompanying drawings, which illustrate, by way of example, the principals of the invention.

BRIEF DESCRIPTION OF THE DRAWINGS

The foregoing features of the present disclosure will become more readily apparent and will be better understood by referring to the following detailed description of preferred embodiments, which are described hereinbelow with reference to the drawings wherein:

FIGS. 1-2 are perspective views of a cannula assembly and a seal assembly in accordance with the principles of the present disclosure;

FIGS. 6-7 are top and bottom perspective views of the gimbal mount of the seal assembly in accordance with the embodiment of FIGS. 1-5C;

FIGS. 8-9 are cross-sectional views of the gimbal mount in accordance with the embodiment of FIGS. 1-7;

DETAILED DESCRIPTION OF PREFERRED EMBODIMENTS

Figure 3:
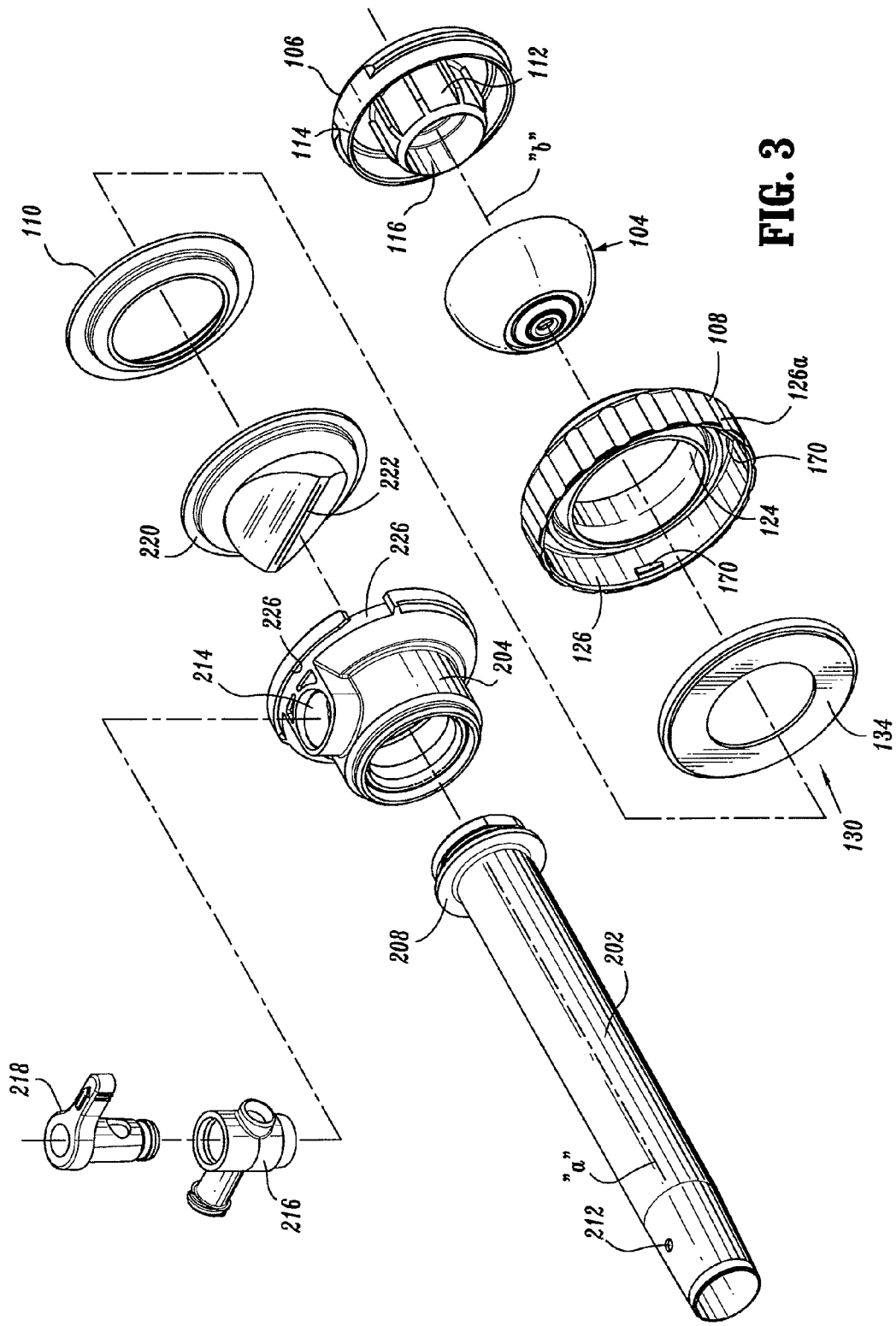
FIG. 3 is a perspective view with parts separated of the cannula and seal assemblies of FIG. 1 in accordance with the embodiment of FIGS. 1-2.

The seal assembly of the present disclosure, either alone or in combination with a seal system internal to a cannula assembly, provides a substantial seal between a body cavity of a patient and the outside atmosphere before, during and after insertion of an instrument through the cannula assembly. Moreover, the seal assembly of the present invention is capable of accommodating instruments of varying diameters, e.g., from 5 mm to 15 mm, by providing a gas tight seal with each instrument when inserted. The flexibility of the present seal assembly greatly facilitates endoscopic surgery where a variety of instruments having differing diameters are often needed during a single surgical procedure.

The seal assembly contemplates the introduction and manipulation of various types of instrumentation adapted for insertion through a trocar and/or cannula assembly while maintaining a fluid tight interface about the instrumentation to preserve the atmospheric integrity of a surgical procedure from gas and/or fluid leakage. Specifically, the seal assembly accommodates angular manipulation of the surgical instrument relative to the seal housing axis. This feature of the present disclosure desirably minimizes the entry and exit of gases and/or fluids to/from the body cavity. Examples of instrumentation include clip appliers, graspers, dissectors, retractors, staplers, laser probes, photographic devices, endoscopes and laparoscopes, tubes, and the like. Such instruments will be collectively referred to herein as "instruments or instrumentation".

By virtue of its features, the seal assembly further defines a substantially reduced profile when assembled together and mounted to a cannula assembly. This reduced profile advantageously increases the working length of instruments introduced into the body cavity through the cannula assembly. In addition, the reduced profile permits enhanced angulation of a surgical instrument relative to the seal housing axis.

In the following description, as is traditional the term "proximal" refers to the portion of the instrument closest to the operator while the term "distal" refers to the portion of the instrument remote from the operator.

Referring now to the drawings, in which like reference numerals identify identical or substantially similar parts throughout the several views, FIGS. 1-2 illustrate the seal assembly 100 of the present disclosure mounted to cannula assembly 200. Cannula assembly 200 may be any conventional cannula suitable for the intended purpose of accessing a body cavity and permit introduction of instruments therethrough. Cannula assembly 200 is particularly adapted for use in laparoscopic surgery where the peritoneal cavity is insufflated with a suitable gas, e.g., $CO_2$, to raise the cavity wall from the internal organs therein. Cannula assembly 200 is typically used with an obturator assembly (not shown) which is a sharp pointed instrument positionable within the passageway of the cannula assembly 200. The obturator assembly is utilized to penetrate the abdominal wall and then subsequently removed from the cannula assembly 200 to permit introduction of the surgical instrumentation utilized to perform the procedure.

With reference to FIGS. 1-4, cannula assembly 200 includes cannula sleeve 202 and cannula housing 204 mounted to an end of the sleeve 202. Any means for mounting cannula sleeve 202 to cannula housing 204 are envisioned including threaded arrangements, bayonet coupling, snap-fit arrangements, adhesives, etc. Cannula sleeve 2-2 and cannula housing 204 may be integrally formed. Cannula sleeve 202 defines a longitudinal axis "a" extending along the length of sleeve 202. Sleeve 202 further defines an internal longitudinal passage 206 dimensioned to permit passage of surgical instrumentation. Sleeve 202 defines collar 208 which is mounted to cannula housing 202 and an inner tapered wall 210 adjacent the collar 208. The sloped configuration of tapered wall 210 may assist in guiding the inserted instrument into longitudinal passage 206. Adjacent the distal end of cannula sleeve 202 is aperture 212 which extends through the wall of the sleeve 202. Aperture 212 permits passage of insufflation gases through cannula sleeve 202 during the surgical procedure. Sleeve 202 may be formed of stainless steel or other rigid materials such as a polymeric material or the like. Sleeve 202 may be clear or opaque. The diameter of sleeve 202 may vary, but, typically ranges from about 10 mm to about 15 mm for use with the seal assembly 100 of the present disclosure.

Cannula housing 204 includes port opening 214 and luer fitting 216 positioned within the port opening 214. Luer fitting 216 is adapted for connection to a supply of insufflation gaseous is conventional in the art and incorporates valve 218 to selectively open and close the passage of the luer fitting 216. Cannula housing 204 further includes duckbill or zero closure valve 220 which tapers distally and inwardly to a sealed configuration. Closure valve 220 defines slit 222 which opens to permit passage of the surgical instrumentation and closes in the absence of the instrumentation. Closure valve 220 is preferably adapted to close upon exposure to the forces exerted by the insufflation gases in the internal cavity. Other zero closure valves are also contemplated including single or multiple slit valve arrangements, trumpet valves, flapper valves, etc. Closure valve 220 rests upon internal shelf 224 of cannula housing 204 when assembled.

Cannula housing 204 includes at least one locking recess 226 preferably two recesses arranged in diametrical opposed relation. Locking recesses 226 serve to releasably secure seal assembly 100 to cannula assembly 200.

With continued reference to FIGS. 1-4, seal assembly 100 will be discussed in detail. Seal assembly 100 may be a separate component from cannula assembly 200 and, accordingly, adapted for releasable connection to the cannula assembly 200. Alternatively, seal assembly 100 may be incorporated as part of cannula assembly 200. Seal assembly 100 includes a seal housing, generally identified as reference numeral 102, and gimbal mount 104 which is disposed within the seal housing 102. Seal housing 102 houses the sealing components of the assembly and defines the outer valve or seal body of the seal assembly 100. Seal housing 102 defines central seal housing axis "b" which is preferably parallel to the axis "a" of cannula sleeve 202 and, more specifically, coincident with the axis "a" of the cannula sleeve 202. Seal housing 102 incorporates three housing components, namely, first, second and third housing components 106, 108, 110, respectively, which, when assembled together, form the seal housing 102. Assembly of housing components 106, 108, 110 may be affected by any of the aforementioned connection means discussed with respect to cannula housing 204.

Figure 4:
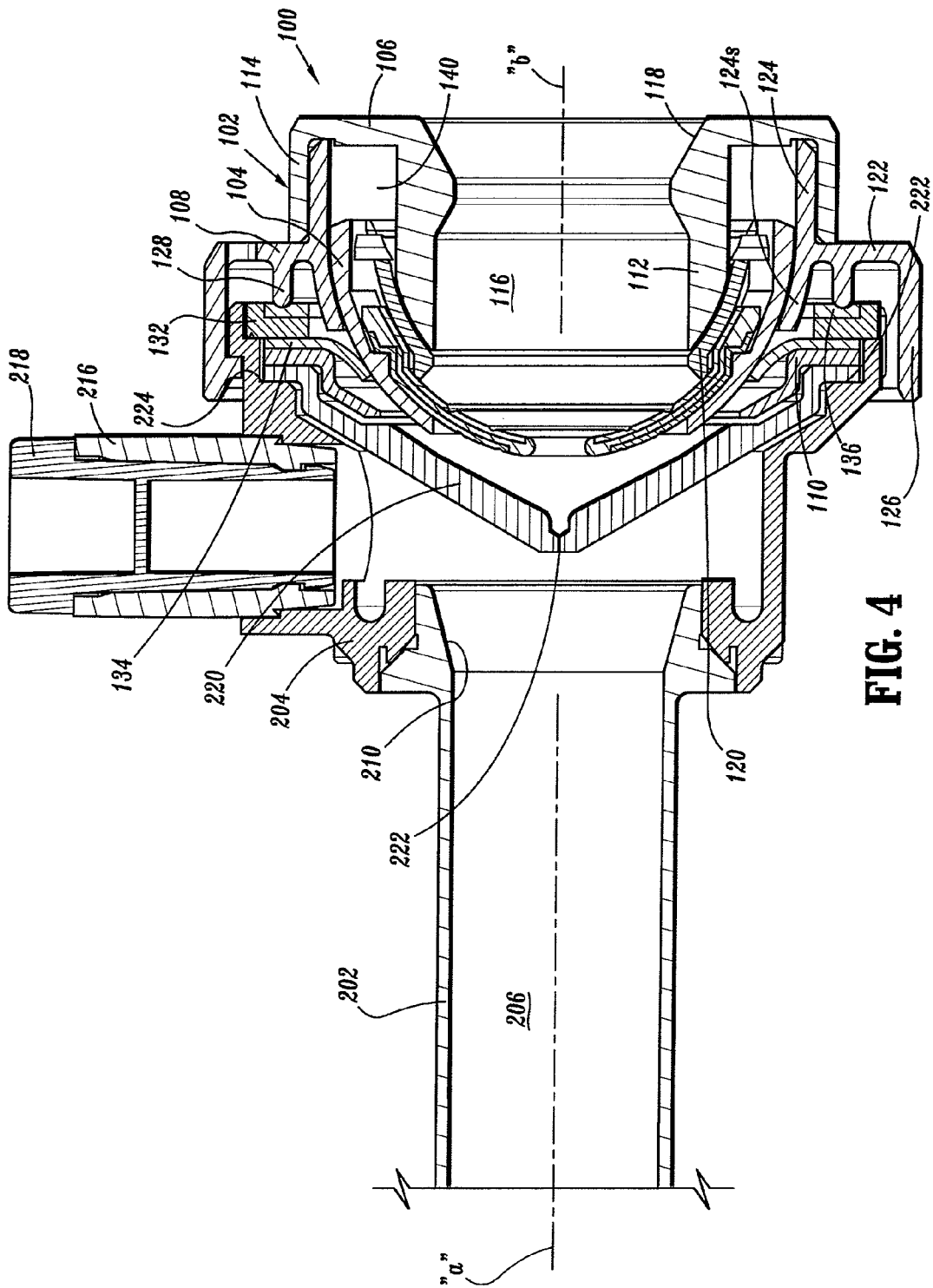
FIG. 4 is a side cross-sectional view of the cannula and seal assemblies in accordance with the embodiment of FIGS. 1-3.

First housing component 106 defines inner guide wall 112 and outer wall 114 disposed radially outwardly of the inner guide wall 112. Inner guide wall 112 defines central passage 116 which is dimensioned to receive a surgical instrument and laterally confine the instrument within seal housing 102. As best shown in FIG. 4, inner guide wall 112 defines sloped or tapered portion 118 adjacent its proximal end. Sloped portion 118 is obliquely arranged relative to seal housing axis "b" and extends radially inwardly relative to the seal housing axis "b" in the distal direction. Sloped portion 118 assists in guiding the inserted instrument into central passage 116, particularly, when the instrument is non-aligned or off-axis relative to the seal housing axis "b", or introduced at an angle relative to the seal housing axis "b". Sloped portion 118 provides more flexibility to the surgeon by removing the necessity that the instrument be substantially aligned with the seal housing axis "b" upon insertion. Inner guide wall 112 is generally cylindrical in configuration and terminates in a distal arcuate or rounded surface 120.

Second housing component 108 includes transverse wall 122, inner cylindrical wall 124 depending in a proximal direction outwardly from the transverse wall 120 and outer wall 126 depending in a distal direction outwardly from the transverse wall 120. Inner cylindrical wall 124 is dimensioned to mate with outer wall 114 of first housing component 106, i.e., in a manner to be positioned within the interior of the outer wall 114 in frictional relation therewith. In the alternative, outer wall 114 of first housing component 106 may be adhered to inner cylindrical wall 124 of second housing component 108. Outer wall 126 defines scalloped outer surface 126a which is dimensioned for gripping engagement by the user. Extending contiguously from inner cylindrical wall 124 in the distal direction is an arcuate or cup shaped gimbal wall support 124s which supports gimbal mount 104. Transverse wall 120 further includes intermediate wall 128 of cylindrical configuration, which is disposed between outer wall 126 and gimbal wall support 124s.

Figure 5B:
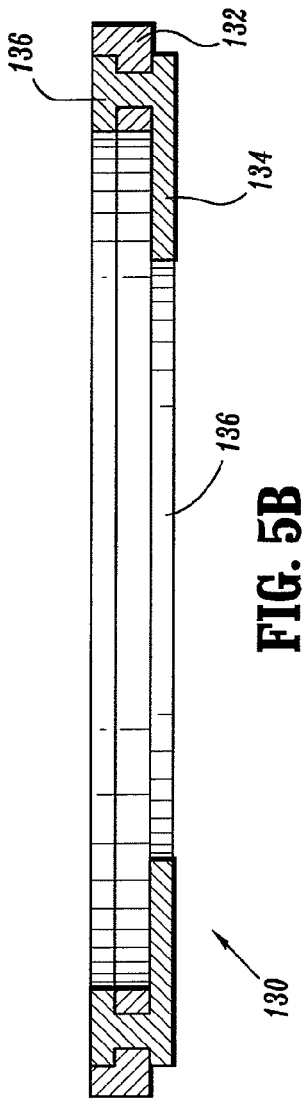
FIG. 5B is a cross-sectional view of the interface seal taken along section lines 5B-5B of FIG. 5A illustrating the interface seal mount and the interface seal member of the seal assembly in accordance with the embodiment of FIGS. 1-5A.
Figure 5C:
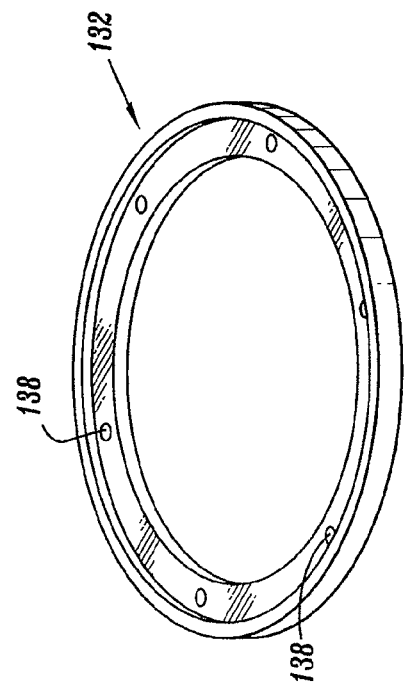
FIG. 5C is a perspective view of the interface seal mount of the interface seal in accordance with the embodiment of FIGS. 1-5B.
Figure 5A:
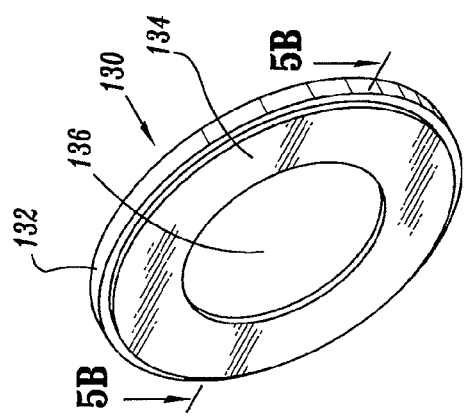
FIG. 5A is a perspective view of the interface seal of the seal assembly in accordance with the embodiment of FIGS. 1-4.
Figure 10:
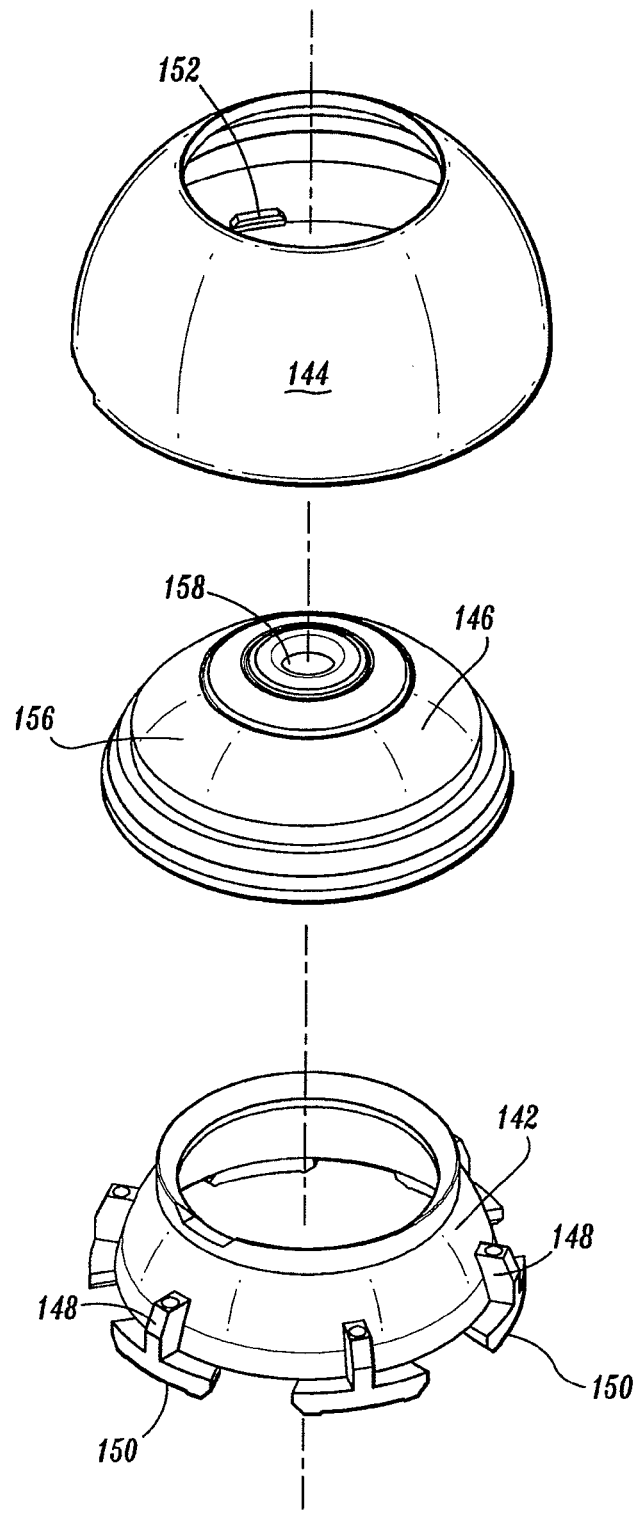
FIG. 10 is a perspective view illustrating the components of the gimbal mount in accordance with the embodiment of FIGS. 1-9.

Referring now to FIGS. 3-4, in conjunction with FIGS. 5A-5C, seal assembly 100 further includes interface seal 130 mounted adjacent gimbal mount 104. Interface seal 130 functions in minimizing the loss of insufflation gases through seal assembly 100. Interface seal 130 includes interface seal mount 132 and flexible interface seal member 134 secured to the seal mount 132. Seal mount 132 is preferably annular in configuration and is fabricated from a relatively rigid material such as a polymeric material or stainless steel. Interface seal member 134 is preferably fabricated from an elastomeric material having qualities to engage seal mount 104 in substantial sealed relation therewith. Interface seal member 134 defines central aperture 136 which receives the forward or distal surface of gimbal mount 104. Interface seal member 134 preferably extends radially inwardly and longitudinally relative to seal housing axis "b" when assembled within seal housing 102. This configuration increases the amount of surface area of interface seal member 134 engaging the outer surface of gimbal mount 104 thereby facilitating the formation and maintenance of a seal about the gimbal mount during manipulation of the instrument. Interface seal 130 further includes gasket seal 136 mounted adjacent the proximal side of interface seal mount 132. Gasket seal 136 is in contact with the forward or distal end of intermediate wall 128 of second housing component 108 and serves to form a seal with the intermediate wall to substantially minimize passage of fluids through seal housing 102.

Interface seal member 134 and gasket seal 136 are preferably monolithically formed of the desired elastomeric material. In one preferred arrangement, interface seal 130 is manufactured via a molding process. In this arrangement, interface seal mount 132 may include a plurality of apertures 138. During molding of interface seal 130, apertures 138 permit the elastomeric material to communicate between the proximal and distal sides of interface seal mount 132 to monolithically form interface seal member 134 and gasket seal 136. Alternatively, gasket seal 136 may be a separate component from interface seal member 134 and may be secured to the seal mount 132 by conventional means.

With particular reference to FIG. 4, gimbal mount 104 is accommodated within an annular space 140 defined between inner and outer walls 112, 114 of first housing component 106. Gimbal mount 104 is mounted in a manner which permits angulation and/or rotational movement of the gimbal mount 104 relative to, or about, seal housing axis "b". Specifically, gimbal mount 104 is free to angulate relative to seal housing axis "b" through a range of motion defined within the confines of annular space 140. The range of movement of gimbal mount 104 will be discussed in greater detail hereinbelow. Interface seal 130 is adapted to maintain a sealing relation with gimbal mount 104 upon angular movement thereof.

Referring now to FIGS. 6-10, in conjunction with FIG. 4, the components of gimbal mount 104 will be discussed in further detail. Gimbal mount 104 includes first and second gimbal housings 142, 144 and resilient seal member 146 which is mounted between the housings 142, 144. In a preferred arrangement, first and second gimbal housings 142, 144 and seal member 146 each define a general hemispherical configuration as shown. First gimbal housing 142 is preferably seated within second gimbal housing 144 and secured to the second gimbal housing 144 through a snap fit connection, welding, adhesives, or the like. Preferably, first gimbal housing 142 includes a plurality of mounting legs 148 radially spaced about the outer periphery of the housing component 134. Legs 148 define locking surfaces 150 which extend in general transverse relation to the axis "b" of seal assembly 200. Similarly, second gimbal housing 144 includes a plurality of corresponding locking detents 152 spaced about the interior of the housing 144. Upon insertion of first gimbal housing 142 within second gimbal housing 144, mounting legs 148 slide along locking detents 152 whereby upon clearing the detents 152, locking surfaces 150 of the mounting legs 148 securely engage the locking detents 152 to fix first gimbal housing 142 within second gimbal housing 144 and secure resilient seal member 146 between the components in sandwiched relation. As appreciated, first gimbal housing 142 is desirably sufficiently resilient to deflect upon insertion to permit mounting legs 148 to clear locking detents 152 and return to their initial position to engage the detents 152.

As mentioned hereinabove, seal member 146 of gimbal mount 104 is interposed between first and second gimbal housings 142, 144. Seal member 146 preferably comprises a resilient center material (e.g., polyisoprene or natural rubber) with first and second layers of fabric 154, 156 at the respective proximal and distal surfaces of the resilient material and impregnated with the resilient material. The fabric may be of any suitable fabric for example, a SPANDEX material containing about 20% LYCRA and about 80% NYLON available from Milliken. A suitable seal member or seal type is disclosed in commonly assigned U.S. patent application Ser. No. 09/449,368, filed Nov. 24, 1999, the contents of which are hereby incorporated herein by reference. Seal member 146 defines central aperture 158 for sealed reception of a surgical instrument. In a preferred arrangement, first layer 154 is arranged to extend or overlap into aperture 158. In this manner, the fabric is positioned to engage the surgical instrument upon passage through aperture 158 of seal member 146 thereby protecting the resilient material defining the aperture. This advantageously minimizes the potential of piercing, penetrating or tearing of the resilient material by the instrument. Alternatively, an additional layer of fabric on the proximal surface of seal member 146 may be superposed and arranged to drape within aperture 158. Seal member 146 preferably includes an annular depression 160 on its distal surface, i.e., within second layer 156 of fabric. Depression 160 receives ledge 162 of second gimbal housing 144 to facilitate fixation of seal member 146 between first and second gimbal housings 142, 144.

Although seal member 146 is disclosed as an impregnated fabric arrangement, it is appreciated that other seal types may be used and still achieve the objectives of the present disclosure. Further, FIG. 8 illustrates annular depressions 164, 166 which have been pressed by a molding tool into layer 160. One or more similar depressions may be pressed into layer 160 to assist positioning of fabric during manufacture of seal member 146.

Seal assembly 100 defines a profile or height which is substantially reduced when compared to conventional cannula seal assemblies. In one preferred embodiment, the overall height of seal assembly 100 ranges from about 0.25 inches to about 1.0 inches, preferably, about 0.65 inches. The reduced height provides more operating space above the patient, which is significant, i.e., positioned in the abdomen to access the underlying cavity.

Figure 13:
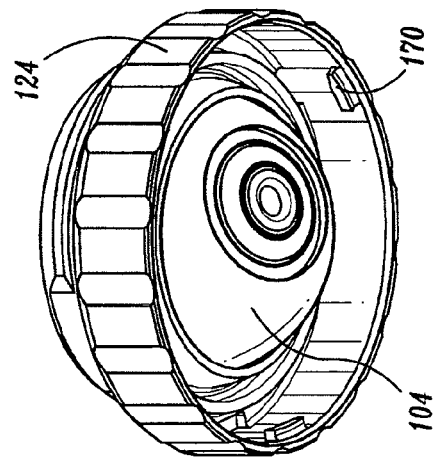
FIGS. 11-13 are perspective views illustrating the range of movement of the gimbal mount within the seal housing in accordance with the embodiment of FIGS. 1-10.
Figure 12:
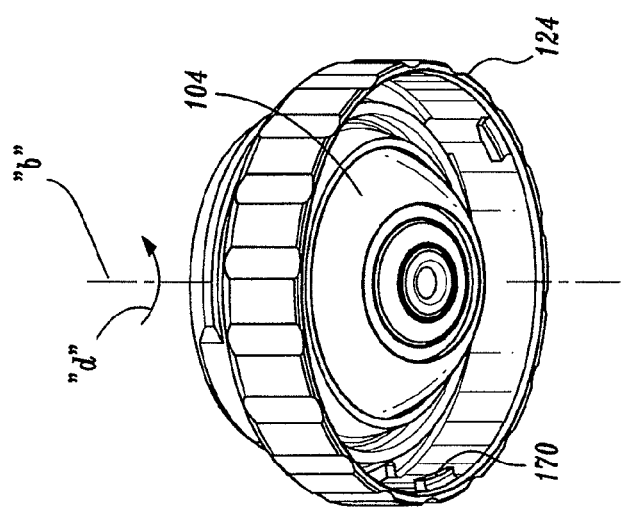
Figure 11:
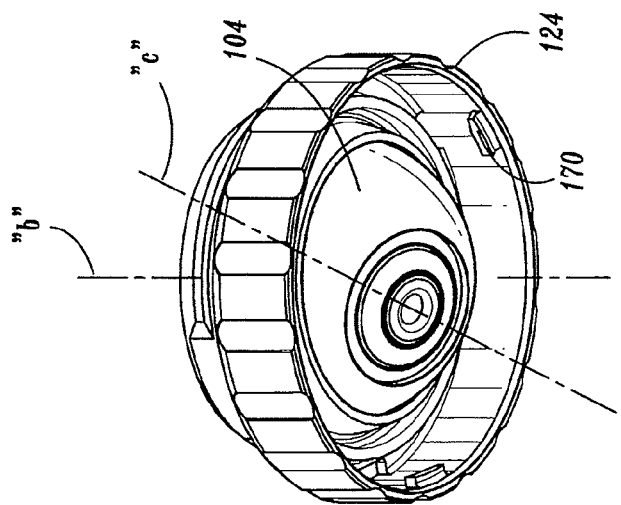
Figure 14:
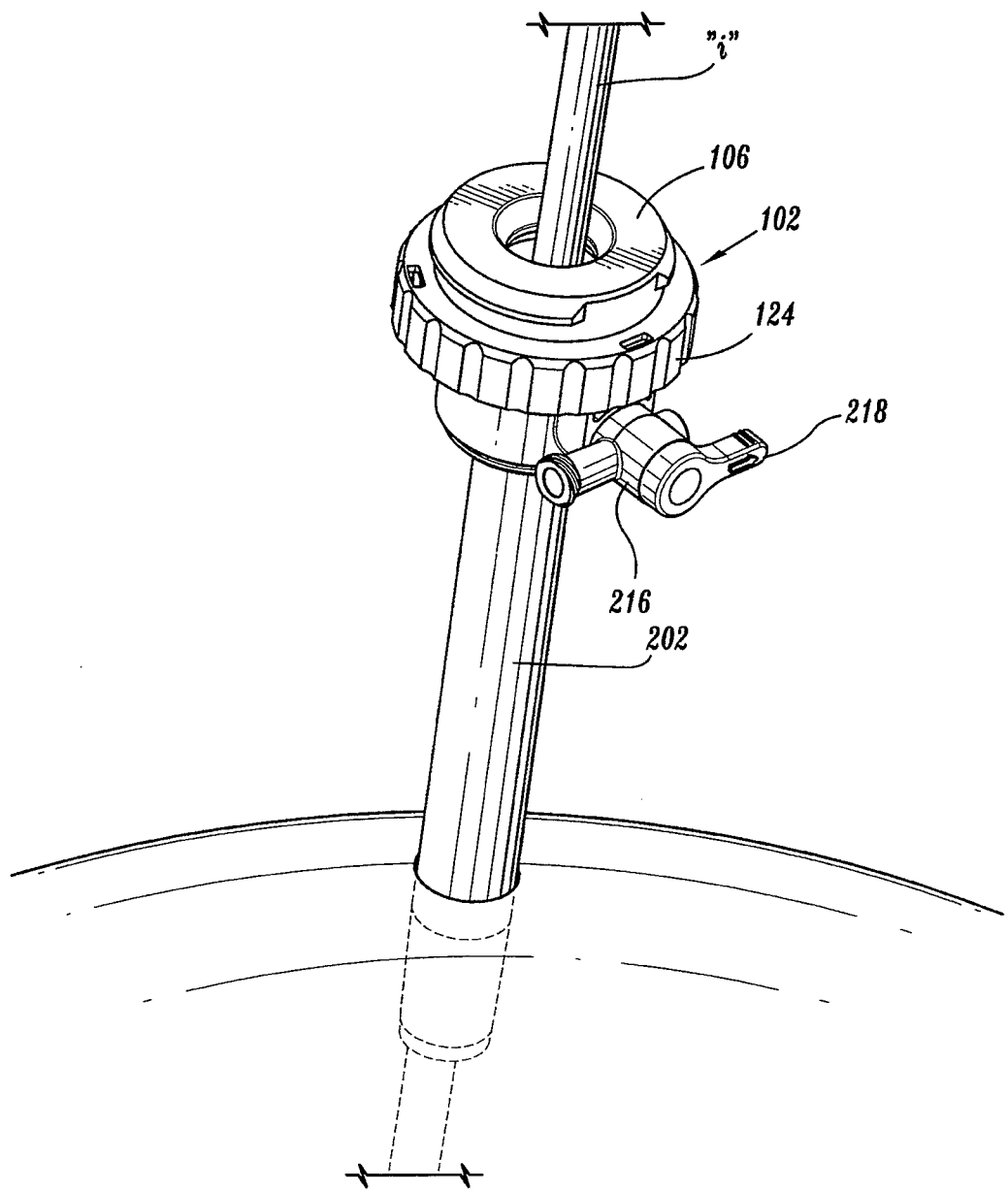
FIG. 14 is a view illustrating the cannula assembly and seal assembly accessing an internal cavity with an instrument introduced therein in accordance with the embodiment of FIGS. 1-13.

With reference now to FIGS. 11-13, in conjunction with FIG. 4, gimbal mount 104 moves within the annular space 140 defined between inner and outer walls 112, 114 to permit angulation of the instrument relative to the seal housing axis "b" and/or rotation about the axis "b" (shown by directional arrow "d") while still maintaining a seal thereabout. During angulation of the instrument, the axis "c" of the aperture 158 of seal member 146 intersects the axis "b" of the seal assembly 100. During angulation, gimbal mount 104 is supported between inner wall 112 and gimbal wall support 124s of seal housing 102. The arcuate inner surface of first gimbal housing 142 rides along distal arcuate surface 120 of inner wall 112 in contacting relation therewith to permit gimbal mount 104 to swivel within seal housing 102. Interface seal member 134 of interface seal 130 permits angular movement of gimbal mount 104 while maintaining the substantial sealing relation with the outer surface of second gimbal housing 144. Lubricant may be provided on the appropriate surfaces to facilitate angulation. In a preferred arrangement, gimbal mount 104 may angulate through an angle inclusive of about 30°, more preferably about 22.5° relative to seal housing axis "b".

Seal assembly 100 may be associated with, or joined to, cannula assembly 200 in a variety of ways. In a preferred embodiment, seal housing 102 of seal assembly 100 and cannula housing 204 of cannula assembly 200 are adapted to detachably engage each other, e.g., through a bayonet lock, threaded connection, or like mechanical means. In one preferred embodiment, second housing component 108 of seal housing 102 includes a plurality of ribs 170 depending radially inwardly from outer wall 24 (FIG. 3). Ribs 170 are received within locking recesses 224 of cannula housing 204, and seal assembly 100 is rotated to secure the ribs 170 beneath the outer wall 226 of cannula housing 204. Other means of joining seal assembly 100 to cannula assembly 200 will be readily apparent to one of ordinary skill in the art.

Figure 15:
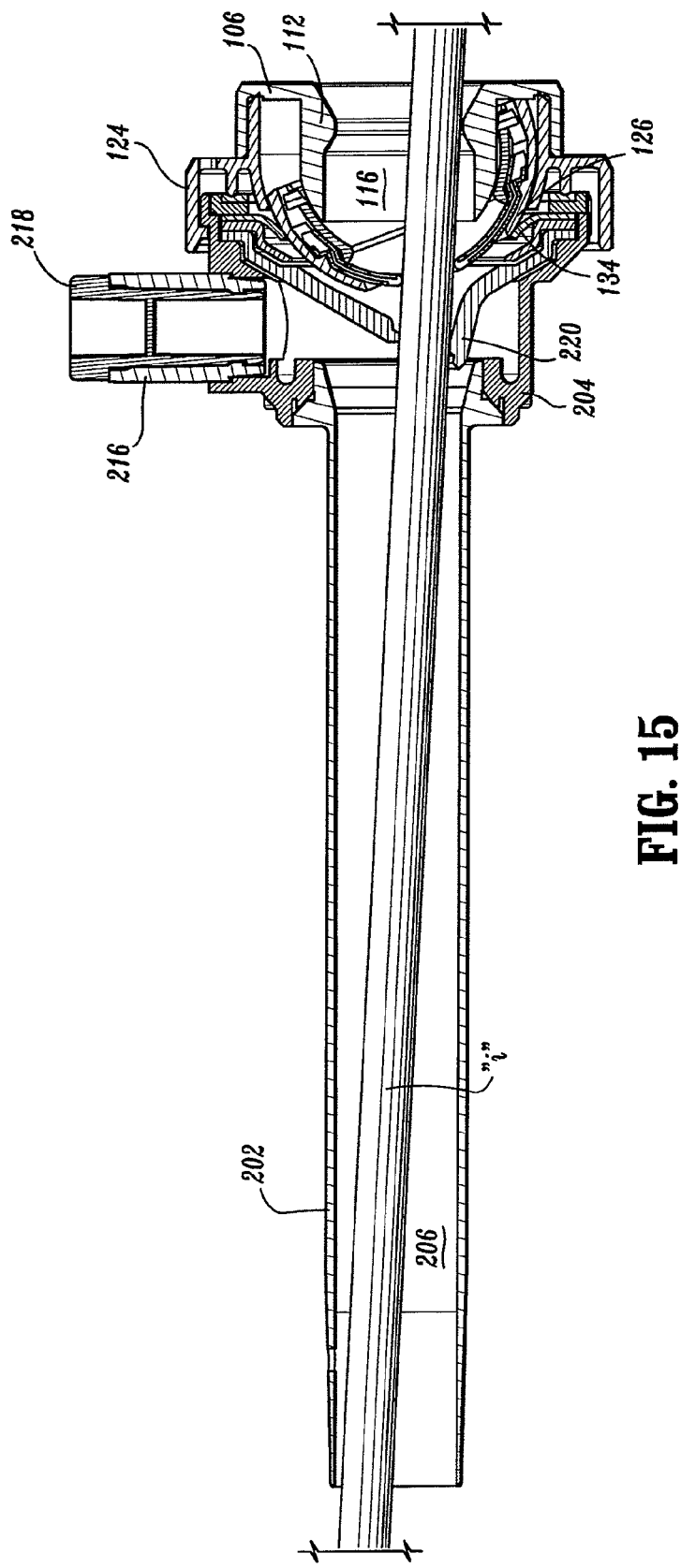
FIG. 15 is a side cross-sectional view of the cannula and seal assemblies illustrating a range of movement of the surgical instrument in accordance with the embodiment of FIGS. 1-14.

Referring now to FIG. 15, use of the seal assembly 100 and cannula assembly 200 in connection with introduction of a surgical instrument will be discussed. Seal assembly 100 is mounted to cannula assembly 200 which may or may not be previously introduced into an insufflated abdominal cavity. An instrument "i" is inserted into seal assembly 100 through passage 116 of inner cylindrical guide wall 112 in seal housing 102. If the axis of the instrument is not perfectly aligned with the axis "a" of cannula assembly 200 or axis "b" of seal assembly 100, then the surgical instrument will contact sloped portion 118 of inner guide wall 112 and/or the inner surface of the seal member 146. Sloped portion 118 guides the instrument into seal housing 102. Contact with seal member 142 can cause some deformation of the seal member 142. The instrument "i" slides along the surface of the gimbal mount 104 and/or the seal member 142 to the aperture 154. The inner seal portions defining aperture 154 stretch to accommodate the instrument diameter, as necessary. The instrument "i" is advanced through aperture 158 of seal member 146 whereby portions of the seal member 146 defining the aperture 158 engage the instrument "i" in sealed relation therewith. The instrument "i" passes further distally into the cannula housing 204 passing through duckbill valve 216 and cannula sleeve 202 into the body cavity. The instrument "i" may be manipulated within seal housing 102 and cannula housing 204. Once the instrument "i" is disposed within the aperture 154, and the friction at the interface seal member 134, gimbal mount 104 and sloped portion 118 is overcome, gimbal mount 104, swivels with respect to seal housing 102 as the instrument is manipulated. Gimbal mount 104 is free to swivel relative to housing 102, while allowing seal member 142 to maintain sealing engagement with the instrument "i" passed therethrough, as well as maintaining the seal around the gimbal mount 104. Preferably, the seal member 142 includes resilient material and fabric material which resists deformation of the aperture 154, as well as tearing of the seal member 142. As discussed, the instrument "i" may be rotated about seal housing axis "b" or pivoted relative to the axis "b" as desired via gimbal mount 104 to perform the surgical procedure. During these manipulations, interface seal member 134 of interface seal 130 maintains a sealing relation with gimbal mount 104.

While the invention has been particularly shown, and described with reference to the preferred embodiments, it will be understood by those skilled in the art that various modifications and changes in form and detail may be made therein without departing from the scope and spirit of the invention. Accordingly, modifications such as those suggested above, but not limited thereto, are to be considered within the scope of the invention.

The invention claimed is:

1. A surgical access device, which comprises:
    a housing defining a central longitudinal axis and having a longitudinal passage to permit passage of a surgical object through the seal housing;
    a seal mount mounted to the seal housing, the seal mount adapted for angular movement relative to the central longitudinal axis and having inners surface portions dimensioned for substantial sealed reception of the surgical object; and
    an interface seal defining an outer seal segment and an inner seal segment extending at least radially inwardly from the outer seal segment and with respect to the central longitudinal axis of the seal housing, the inner seal segment defining a passage which at least partially accommodates the seal mount, the inner seal segment in contacting relation with the seal mount adjacent the passage and dimensioned and adapted to establish and maintain a substantial sealed relation with the seal mount during angular movement thereof; and
    a sleeve extending from the seal housing, the sleeve dimensioned and adapted for passage through body tissue to provide access to an underlying tissue site.

2. The surgical access device according to claim 1 wherein the inner seal segment of the interface defines an opening, the opening being a passage.

3. The surgical access device according to claim 1 wherein the inner seal segment is dimensioned to extend along the central longitudinal axis.

4. The surgical access device according to claim 1 wherein the interface seal includes a relatively rigid interface mount, the interface seal being mounted to the interface mount.

5. The surgical access device according to claim 4 wherein the interface seal includes an annular gasket seal member mounted to the interface mount and positioned to contact an internal surface of the seal housing in substantial sealing relation therewith to form a substantial seal within the seal housing.

6. The surgical access device according to claim 5 wherein the interface seal member and the gasket seal member are monolithically formed.

7. The surgical access device according to claim 1 wherein the seal member of the seal mount includes a resilient member and a protective layer juxtaposed relative to the resilient member.

8. The surgical access device according to claim 7 wherein the protective layer comprises a fabric material.

9. The surgical access device according to claim 1 wherein the seal mount is adapted to rotate about the central longitudinal axis.

10. The surgical access device according to claim 1 including a closure valve dimensioned and adapted to permit passage of the surgical object, and being dimensioned and adapted to be substantially closed in the absence of the surgical object.

11. The surgical access device according to claim 1 wherein the seal mount is detached from the inner seal segment of the seal interface whereby the seal mount is adapted to move relative to the inner seal segment during the angular movement thereof.

* * * * *